US012667371B2

(12) United States Patent
Montero

(10) Patent No.: US 12,667,371 B2
(45) Date of Patent: Jun. 30, 2026

(54) POINTED COUNTERSINK DRILL

(71) Applicant: BIOMET 3I, LLC, Palm Beach Gardens, FL (US)

(72) Inventor: Miguel Montero, Boynton Beach, FL (US)

(73) Assignee: BIOMET 3I, LLC, Palm Beach Gardens, FL (US)

( * ) Notice: Subject to any disclaimer, the term of this patent is extended or adjusted under 35 U.S.C. 154(b) by 0 days.

(21) Appl. No.: 18/815,602

(22) Filed: Aug. 26, 2024

(65) Prior Publication Data

US 2025/0204930 A1      Jun. 26, 2025

Related U.S. Application Data

(60) Provisional application No. 63/535,445, filed on Aug. 30, 2023.

(51) Int. Cl.
*A61B 17/16* (2006.01)
(52) U.S. Cl.
CPC ................................. *A61B 17/1615* (2013.01)
(58) Field of Classification Search
CPC . A61B 17/16; A61B 17/1613; A61B 17/1615; A61B 17/1617; A61B 17/162; A61B 17/1622; A61B 17/1624; A61B 17/1626; A61B 17/1628; A61B 17/1655; A61B 17/1657; A61B 17/1673; A61C 8/0089
See application file for complete search history.

(56) References Cited

U.S. PATENT DOCUMENTS

| | | | | |
|---|---|---|---|---|
| 3,564,945 A | * | 2/1971 | Bradley | ................ B23B 51/009 408/227 |
| 4,341,206 A | | 7/1982 | Perrett et al. | |
| 4,345,899 A | * | 8/1982 | Vlock | ...................... A61C 3/02 433/165 |
| 4,936,721 A | * | 6/1990 | Meyer | .................... B23B 51/08 408/230 |
| 5,055,105 A | | 10/1991 | Hamlin et al. | |
| 6,641,395 B2 | * | 11/2003 | Kumar | ................. A61C 8/0089 433/165 |

(Continued)

FOREIGN PATENT DOCUMENTS

| | | | | |
|---|---|---|---|---|
| CN | 21266187 | | 3/2021 | |
| DE | 102016214386 A1 | * | 1/2018 | ............. B23B 47/34 |

(Continued)

OTHER PUBLICATIONS

Extended European Search Report for European Patent Application No. 24197454.2, dated Nov. 28, 2024 8 pages.

*Primary Examiner* — Eric S Gibson
(74) *Attorney, Agent, or Firm* — Sheridan Ross P.C.

(57) ABSTRACT

Embodiments of the present disclosure include a countersink portion having at least one ridge, the at least one ridge tapering to at least one inflection, the at least one ridge further extending from the at least one inflection toward a drilling portion, thereby forming at least one transition surface; the drilling portion having an elongated pin and a tip; wherein the drilling portion extends from the countersink portion and the at least one transition surface extends between the countersink portion and the tip.

20 Claims, 5 Drawing Sheets

(56)                References Cited

U.S. PATENT DOCUMENTS

| | | | | |
|---|---|---|---|---|
| 6,863,529 B2 * | 3/2005 | Strong | A61C 8/0089 | 433/165 |
| 7,214,009 B2 * | 5/2007 | Quanz | B23G 5/20 | 408/144 |
| 8,029,509 B2 * | 10/2011 | Ducharme | A61B 17/1615 | 606/80 |
| 8,226,654 B2 * | 7/2012 | Ranck | B23B 51/02 | 606/167 |
| 10,729,520 B2 * | 8/2020 | Scalise | A61C 3/02 | |
| 11,045,212 B2 | 6/2021 | Pacaccio et al. | | |
| 11,471,172 B1 * | 10/2022 | Bram | A61B 17/1615 | |
| 12,220,296 B1 * | 2/2025 | Bram | A61B 17/1673 | |
| 2002/0031745 A1 * | 3/2002 | Kumar | A61B 17/1615 | 433/165 |
| 2004/0063067 A1 * | 4/2004 | Takahashi | A61C 8/0089 | 433/165 |
| 2006/0008772 A1 * | 1/2006 | Brajnovic | A61C 8/0089 | 433/165 |
| 2006/0210949 A1 * | 9/2006 | Stoop | A61B 17/1673 | 433/165 |
| 2007/0213736 A1 * | 9/2007 | Ducharme | A61B 17/1615 | 606/80 |
| 2008/0085488 A1 * | 4/2008 | Lazarof | A61B 17/1615 | 433/50 |
| 2009/0067943 A1 * | 3/2009 | Capone | B23B 51/08 | 408/230 |
| 2009/0239200 A1 * | 9/2009 | Brajnovic | A61B 17/1673 | 433/165 |
| 2009/0305189 A1 * | 12/2009 | Scortecci | A61C 8/0089 | 433/165 |
| 2010/0009314 A1 * | 1/2010 | Tardieu | A61C 8/0089 | 433/144 |
| 2010/0112517 A1 * | 5/2010 | Chen | A61B 17/1673 | 433/165 |
| 2010/0145341 A1 * | 6/2010 | Ranck | A61B 17/1615 | 606/167 |
| 2012/0330315 A1 * | 12/2012 | Ranck | B23B 51/02 | 606/80 |
| 2013/0218160 A1 * | 8/2013 | Bjorn | A61B 17/1615 | 606/80 |
| 2014/0127640 A1 * | 5/2014 | Zacharia | A61C 3/02 | 433/82 |
| 2014/0220508 A1 * | 8/2014 | Scalise | A61C 19/02 | 433/173 |
| 2022/0015865 A1 * | 1/2022 | Kim | A61C 8/0089 | |
| 2022/0031425 A1 * | 2/2022 | Gunacar | A61B 17/1673 | |
| 2022/0409333 A1 * | 12/2022 | Lazarovitch | A61B 17/1673 | |
| 2025/0204930 A1 * | 6/2025 | Montero | A61C 8/0089 | |

FOREIGN PATENT DOCUMENTS

| | | | | |
|---|---|---|---|---|
| EP | 0903116 | 3/1999 | | |
| EP | 2953573 B1 * | 1/2020 | | A61C 8/0089 |
| EP | 4516262 A1 * | 3/2025 | | A61B 17/1615 |
| ES | 2775280 T3 * | 7/2020 | | A61B 17/1673 |
| KR | 20210104304 | 8/2021 | | |
| WO | WO-2004058095 A1 * | 7/2004 | | A61C 8/0089 |
| WO | WO-2006120654 A2 * | 11/2006 | | B23B 51/08 |
| WO | WO-2018011314 A1 * | 1/2018 | | B23B 1/009 |
| WO | WO-2019140482 A1 * | 7/2019 | | A61B 17/1615 |

* cited by examiner

POINTED COUNTERSINK DRILL

CROSS-REFERENCE TO RELATED APPLICATION

This application claims the benefit of U.S. Provisional Application No. 63/535,445, filed on Aug. 30, 2023, which is incorporated herein by reference in its entirety.

FIELD

Embodiments of the present disclosure relate generally to tools for drilling into bone, and specifically relate to countersink drills with an extended, pointed, drilling portion.

BACKGROUND

To install dental implants, a cavity for the implant is typically created by drilling through a tooth, or bone. Specifically, countersink drill bits are often used to drill through the alveolar ridge, thereby creating a convenient surface to securely install an implant with minimal pressure. Existing countersink drill bits, however, are often too blunt. For example, following tooth extraction, a small ridge of bone may protrude which may be drilled through prior to implant insertion. Existing countersink drill bits, however, often slide off the small ridge during drilling because the drill bit fails to securely anchor into the bone. This leads to inaccurate drilling and can cause collateral damage to the surrounding bone and soft tissue. Namely, drilling into bone, and the pressure imparted during implant insertion, can result in trauma to the bone structure. This trauma may result in bone resorption, or deterioration, following surgery. Accordingly, while existing countersink drill bits help minimize trauma caused when inserting an implant, they still may produce trauma during the drilling itself. Further, as implant size increases, so does the countersink drill bit, and accordingly the probability of inaccurate drilling and collateral damage.

To improve drilling, surgeons often create a small hole, or pilot hole, in the bone before utilizing a countersink drill bit. This practice, though, requires multiple steps and multiple tools. As a result, surgeons may accidentally use the wrong countersink drill bit or may misalign the countersink drill bit with the pilot hole.

SUMMARY

In this regard, it is beneficial to provide a single instrument comprising a countersink drill bit with sufficient guidance to minimize collateral impact when drilling. The following disclosure describes at least one embodiment of a drill bit having a countersink portion and an elongated, pointed, drilling portion. Further, the countersink portion engages a shaft and the shaft has a shank operable to engage a drill. Specific embodiments utilize various transitions between the countersink portion and drilling portion, relative lengths of the drilling portion compared to the countersink portion, relative widths between the countersink portion and drilling portion, different countersink angles, and/or different drill point angles.

It is at least one aspect of the present disclosure to provide a single instrument, or drill bit, that can be used to drill into bone accurately and safely. In some embodiments, the drill bit is sized for dental surgery. The drill bit comprises a countersink portion and a drilling portion and the drilling portion is substantially pointed, or has an elongated pin.

Namely, the drilling portion may be characterized by an elongated pin. The drilling portion is operable to pierce the drilling surface and produce a pilot hole, starter hole, or guide hole. Since the drilling portion is substantially pointed, the drilling portion can pierce a variety of drilling surfaces and can establish a pilot hole with sufficient depth and width. Accordingly, the drilling portion sufficiently anchors the drill bit into bone, particularly protruding or non-uniform surfaces Further, the drilling portion engages the countersink portion, so the countersink portion immediately enters the pilot hole created by the drilling portion. Accordingly, the countersink portion will enter the bone with the desired alignment and with minimal collateral impact relative to existing countersink drill bits. Thus, the countersink portion shapes the cavity for implant insertion with minimal trauma to the affected area.

The phrases "at least one," "one or more," and "and/or," as used herein, are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B, and C together.

Unless otherwise indicated, all numbers expressing quantities, dimensions, conditions, and so forth used in the specification and claims are to be understood as being modified in all instances by the term "about".

The term "a" or "an" entity, as used herein, refers to one or more of that entity. As such, the terms "a" (or "an"), "one or more," and "at least one" can be used interchangeably herein.

Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Accordingly, the terms "including," "comprising," or "having" and variations thereof can be used interchangeably herein. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

It shall be understood that the term "means" as used herein shall be given its broadest possible interpretation in accordance with 35 U.S.C. § 112(f). Accordingly, a claim incorporating the term "means" shall cover all structures, materials, or acts set forth herein, and all of the equivalents thereof. Further, the structures, materials, or acts and the equivalents thereof shall include all those described in the summary of the invention, brief description of the drawings, detailed description, abstract, and claims themselves.

These and other advantages will be apparent from the disclosure of the embodiments contained herein. The above-described embodiments, objectives, and configurations are neither complete nor exhaustive. The Summary is neither intended nor should it be construed as being representative of the full extent and scope of the present disclosure. Moreover, references made herein to "the present disclosure" or aspects thereof should be understood to mean certain embodiments and should not necessarily be construed as limiting all embodiments to a particular description. The present disclosure is set forth in various levels of detail in the Summary as well as in the attached drawings and the Detailed Description and no limitation as to the scope of the present disclosure is intended by either the inclusion or non-inclusion of elements, components, etc. in this Summary. Additional aspects of the present disclosure will become more readily apparent from the Detailed Description, particularly when taken together with the drawings.

It is to be appreciated that any feature described herein can be claimed in combination with any other feature(s) as described herein, regardless of whether the features come from the same described embodiment.

Any one or more aspects described herein can be combined with any other one or more aspects described herein. Any one or more features described herein can be combined with any other one or more features described herein. Any one or more embodiments described herein can be combined with any other one or more embodiments described herein.

The use of "substantially" in the present disclosure, when referring to a measurable quantity (e.g., a diameter or other distance) and used for purposes of comparison, is intended to mean within 10% of the comparative quantity. The terms "substantially similar to," "substantially the same as," and "substantially equal to," as used herein, should be interpreted as if explicitly reciting and encompassing the special case in which the items of comparison are "similar to," "the same as" and "equal to," respectively.

As used herein, unless otherwise specified, the terms "about," "approximately," etc., when used in relation to numerical limitations or ranges, mean that the recited limitation or range may vary by up to 10%. By way of non-limiting example, "about 750" can mean as little as 675 or as much as 825, or any value therebetween. When used in relation to ratios or relationships between two or more numerical limitations or ranges, the terms "about," "approximately," etc. mean that each of the limitations or ranges may vary by up to 10%; by way of non-limiting example, a statement that two quantities are "approximately equal" can mean that a ratio between the two quantities is as little as 0.9:1.1 or as much as 1.1:0.9 (or any value therebetween).

While specific embodiments and applications have been illustrated and described, the present disclosure is not limited to the precise configuration and components described herein. Various modifications, changes, and variations which will be apparent to those skilled in the art may be made in the arrangement, operation, and details of the methods and systems disclosed herein without departing from the spirit and scope of the overall disclosure.

BRIEF DESCRIPTION OF THE DRAWINGS

Those of skill in the art will recognize that the following description is merely illustrative of the principles of the disclosure, which may be applied in various ways to provide many different alternative embodiments. This description is made for illustrating the general principles of the teachings of this disclosure and is not meant to limit the inventive concepts disclosed herein.

The accompanying drawings, which are incorporated in and constitute a part of the specification, illustrate embodiments of the disclosure and together with the general description of the disclosure given above and the detailed description of the drawings given below, serve to explain the principles of the disclosure.

Figures 1, 2:
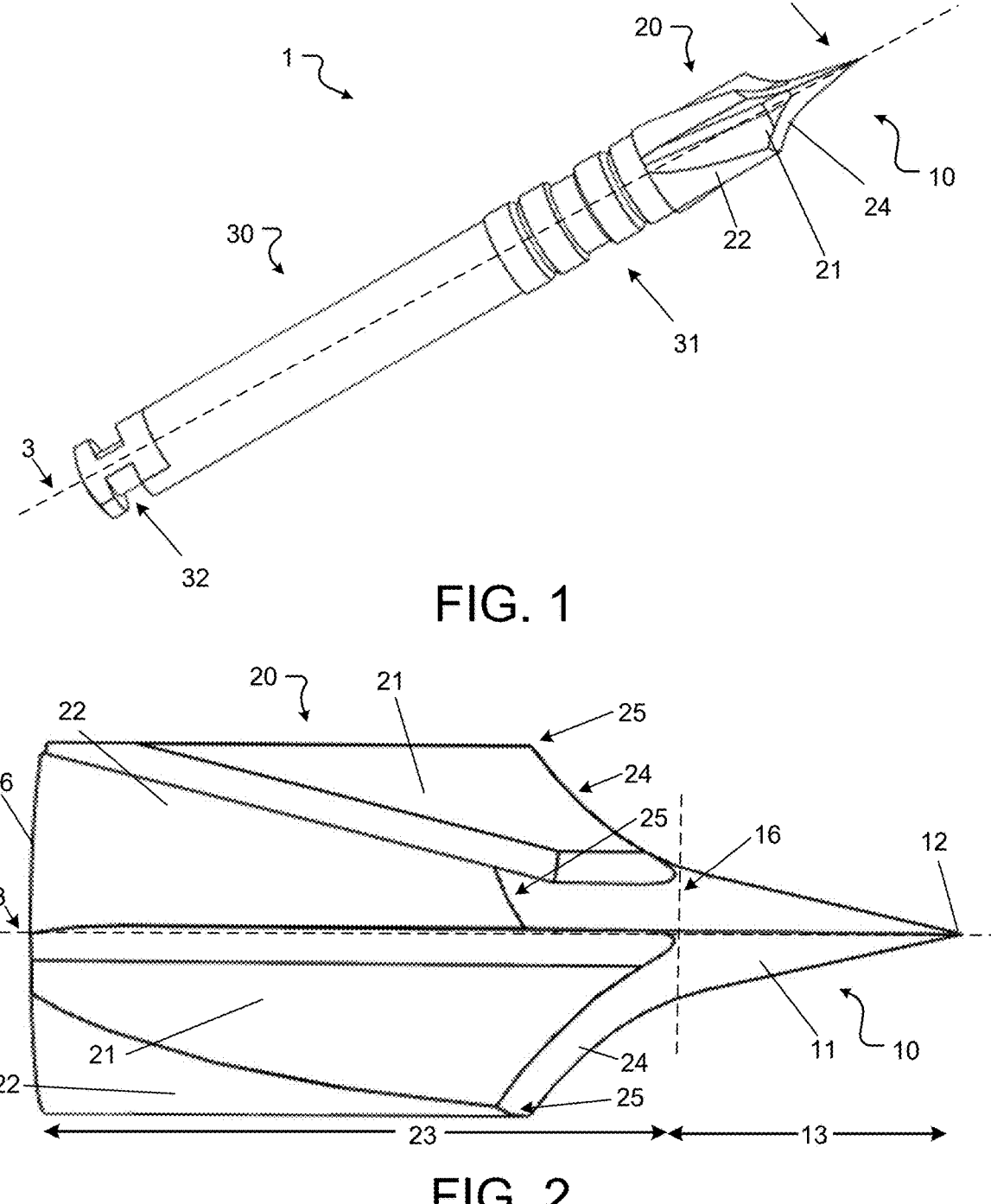
FIG. 1 is a perspective view of a drill bit according to an embodiment of the present disclosure.
FIG. 2 is front view of a segment of a drill bit according to an embodiment of the present disclosure.

It should be understood that the drawings are not necessarily to scale, and various dimensions may be altered. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION

Unless defined otherwise, all technical and scientific terms used herein have the same meaning as is commonly understood by one of ordinary skill in the art. All patents, applications, published applications, and other publications to which reference is made herein are incorporated by reference in their entirety. If there is a plurality of definitions for a term herein, the definition provided in the Summary prevails unless otherwise stated.

Although the following text sets forth a detailed description of numerous different embodiments, it should be understood that the legal scope of the description is defined by the words of the claims set forth at the end of this disclosure. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways.

Generally, the present disclosure concerns a drill bit comprising a drilling portion and a countersink portion. The drilling portion can be substantially pointed such that it has an elongated pin. Specifically, the drilling portion is operable to securely engage non-uniform drilling surfaces, such as small portions of bone, protrusions, ridges, etc. For example, following tooth extraction, a small ridge of bone may protrude from the gums. The drilling portion may securely engage the protruding ridge with minimal impact to the surrounding bone and soft tissue because the drilling portion is sufficiently pointed. Further, upon entry into the bone, the drilling portion is operable to establish a guide for ensuing drilling, such as by a countersink drilling portion. Namely, since the drilling portion is elongated, a sufficiently deep guide, or pilot hole, may be created.

Further, the drilling portion extends from the countersink portion. Specifically, the countersink portion tapers into the drilling portion, providing a smooth transition between the drilling portion and countersink portion. The smooth transition encourages continued alignment during drilling. The countersink portion is operable to follow the guide created by the drilling portion and create a cavity for implant insertion. For example, the countersink portion may create a chamfered cavity such that an implant can be inserted with minimal pressure exerted to the surrounding bone and soft tissue.

Combined in a single instrument, the drilling portion and countersink portion minimize impact to surrounding bone and soft tissue when drilling into a bone for implant insertion. Specifically, the drilling portion facilitates accurate, and stable entrance into the bone. Further, the countersink portion, immediately guided by the drilling portion, creates a desirable cavity for implant insertion. Also, the taper from the countersink portion into the drilling portion provides a smooth, or continuous, transition between drilling and countersink, thereby minimizing the potential for wobbling, shifting, or misalignment. Accordingly, the continuous, as opposed to stepped, transition between the countersink portion and drilling portion further encourages accurate, minimally invasive drilling.

Further, the countersink portion extends from a shaft, which has a shank at a distal end. The shank is operable to engage a chuck on a drill and thus simultaneously rotate the countersink portion and drilling portion. Namely, since the shaft, countersink portion, and drilling portion are integrated, the drilling portion and countersink portion rotate together. Accordingly, the countersink portion can immediately follow the guide, or pilot hole, created by the pointed drilling portion. Therefore, proper alignment of the countersink portion is encouraged and impact to surrounding bone and soft tissue is minimized.

Turning to FIG. 1, a drill bit 1 comprising a drilling portion 10, a countersink portion 20, and a shaft 30 is shown. As illustrated in FIG. 1, the drilling portion has an elongated pin 11. Namely, the drilling portion 10 is substantially elongated and pointed relative to conventional countersink drill bits. It will be appreciated that in other embodiments the drilling portion 10 may be any shape, size, and/or have any cross-sectional shape (e.g., an elongated pin with a star cross-section, a triangular cross-section, etc.). Further, the drilling portion 10 extends from the countersink portion 20. Specifically, the countersink portion 20 comprises at least one ridge 22 defining at least one flute 21 therebetween. The at least one flute 21 is operable to remove portions of the cutting surface of, for example, bone during rotation. Specifically, the at least one flute 21 increases drilling speed and efficiency by removing pieces of the drilling surface that may otherwise lead to clogging of debris. The at least one flute 21 is further operable to provide channels for air flow, thereby cooling the drill bit during operation.

While the embodiment of the present disclosure illustrated in FIG. 1 comprises four flutes, alternative embodiments may comprise different amounts, and configurations of flutes. For example, in some embodiments, the countersink portion 20 comprises one flute, two flutes, or more than two flutes. In further embodiments, the drill bit 1 may not have any flutes. In such embodiments, the at least one ridge 22 may continuously wrap around the countersink portion 20. The selection of the number of flutes, and the corresponding configuration may be based on, for example, whether drilling fluid is used, or manufacturing complexity.

Further, the at least one ridge 22 comprises at least one transition surface 24. The at least one transition surface 24 tapers toward the drilling portion 10. For example, as shown in FIG. 1, the drill bit may comprise at least four transition surfaces 24, wherein each transition surface 24 tapers toward the drilling portion 10. The at least one transition surface 24 provides a smooth and continuous, as opposed to stepped, transition between the drilling portion 10 and countersink portion 20. The smooth transition stabilizes entry of the countersink portion 20 into the bone, thereby improving drilling accuracy and mitigating impact to surrounding bone and soft tissue.

While FIG. 1 illustrates transition surfaces 24 that are concave, alternative embodiments may comprise at least one substantially planar surface, or at least one substantially convex surface, or a combination thereof. Ultimately, the curvature of the at least one transition surface 24, or lack thereof, may be based on implant size, drilling surface, and/or manufacturing complexity.

With continued reference to FIG. 1, the drill bit 1 further comprises a shaft 30. The shaft 30 extends from the countersink portion 20 away from the drilling portion 10. The shaft 30 may be primarily cylindrical, as shown in FIG. 1. In alternative embodiments, the shaft's 30 cross section may be defined by a rectangle, square, trapezoid, or any other cross-section known to form a shaft. The shaft 30 may form a complementary geometry to a chuck engaging a drill. In other words, the shaft 30 comprises a shank 32 which is operable to engage a chuck and secure the drill bit 1 in a drill. Further, the shaft 30 may comprise at least one groove 31. The at least one groove 31 may visually indicate drilling depth during an operation. Accordingly, the at least one groove 31 may mitigate the risk of drilling too deep and impacting surrounding bone and soft tissue. FIG. 1 provides a wide view of the present disclosure, but the countersink portion 20 and drilling portion 10 comprise other features to improve drilling accuracy and limit collateral impact.

For example, referencing FIG. 2, the countersink portion comprises at least one inflection 25. Specifically, the at least one ridge 22 tapers from a base of the countersink portion 26 toward the at least one inflection 25.

As illustrated in FIG. 2, the at least one inflection 25 may be an inflection edge having a sharp corner with minimal radius. In alternative embodiments, the at least one inflection may comprise a larger radius or radii than shown in FIG. 2.

Further, the at least one inflection 25 delineates a portion of the at least one ridge 22 where the at least one ridge 22 extends toward a longitudinal axis 3 of the drill bit 1. Namely, beyond the at least one inflection 25, toward the drilling portion 10, the at least one ridge 22 extends toward the longitudinal axis 3 of the drill bit 1 and tapers toward the drilling portion 10, thereby defining at least one transition surface 24. Further, the drilling portion 10 comprises a drilling portion base 16. Specifically, the drilling portion base 16 defines the start of the drilling portion 10 proximate the at least one ridge 22 of the countersink portion 20. The drilling portion base 16 is defined by a plane tangent to the outermost edge of the at least one ridge 22.

In the embodiment illustrated in FIG. 2, the curvature of the at least one transition surface 24 extends to form part of the drilling portion 10. Namely, the curvature of the at least one transition surface 24 extends beyond the drilling portion base 16 toward a linearly tapered section of the drilling portion 10. In alternative embodiments, however, the curvature of the at least one transition surface 24 may terminate at the drilling portion base 16. In such embodiments, the drilling portion may comprise a separate curvature from the curvature of the at least one transition surface 24 that leads into a linearly tapered section of the drilling portion 10. Alternatively, the drilling portion 10 may have a consistent linear taper from the drilling portion base 16 to the drilling portion tip 12.

Further, as shown in FIG. 2, the drilling portion 10 is relatively long compared to the countersink portion 20.

Specifically, while the drilling portion 10 is shorter than the countersink portion 20 in FIG. 2, it is not as relatively short as conventional in the art. A relatively long drilling portion 10 establishes a sufficient guide or pilot hole for the countersink portion 20 to follow. If the drilling portion 10 has a minor or negligible length compared to the countersink portion 20, as common in the art, then there may be increased risk of the countersink portion 20 misaligning with the cutting surface of, for example, a bone. Accordingly, the relatively long drilling portion increases accuracy and stability, thereby minimizing impact to surrounding bone and soft tissue.

Namely, the drilling portion 10 comprises a drilling portion length 13, defined as the distance along the longitudinal axis 3 between the drilling portion base 16 and the drilling portion tip 12. Additionally, the countersink portion 20 comprises a countersink portion length 23, defined as the distance along the longitudinal axis 3 between the countersink portion base 26 and the drilling portion base 16. Further, the present embodiment comprises a ratio between the countersink portion length 23 and the drilling portion length 13. If the drilling portion length 13 were minor or negligible relative to the countersink portion length 23, as is common in the art, then the ratio between the countersink portion length 23 and the drilling portion length 13 would be very large (e.g., greater than 10). The present embodiment, however, comprises a ratio between the drilling portion length that is less than approximately 5.

Further, if the drilling portion length 13 was substantially larger than the countersink portion length 23 (e.g., ratio between the countersink portion length 23 and drilling portion length 13 is less than 0.25) then the drilling portion 10 may be too long to reliably guide the countersink portion 20. Namely, if the drilling portion 10 is too long, then the drilling portion 10 has an increased risk of drifting, shifting, and/or misaligning, when progressing through a bone. Further, when operating on small regions of bone, such as those encountered during dental surgery, a relatively long drilling portion 10 may be inefficient. For example, if the drilling portion 10 were substantially longer than the countersink portion 20, then the drilling portion 10 may be impacting more of the bone than necessary to guide the countersink portion 20, thereby increasing the risk of impacting surrounding bone and soft tissue. Accordingly, the present embodiment comprises a ratio between the countersink portion length 23 and the drilling portion length 13 that is between 0.9 and 5.

In some embodiments, the ratio between the countersink portion length 23 and the drilling portion length 13 is between 1 and 3, or between 2 and 4, or between 3 and 5. In further embodiments, the ratio between the countersink portion length 23 and the drilling portion length 13 is between approximately 1 and 1.5, or between approximately 1.5 and 2, or between approximately 2 and 2.5, or between approximately 2.5 and 3, or between approximately 3 and 3.5, or between approximately 3.5 and 4, or between approximately 4 and 4.5, or between approximately 4.5 and 5. The relationship between the countersink portion length 23 and drilling portion length 13 is important to minimize collateral impact to surrounding bone and soft tissue during drilling. To further mitigate damage to surrounding bone and soft tissue, the drilling portion 10 comprises a base width 17 operable to guide the countersink portion 20.

Figure 3:
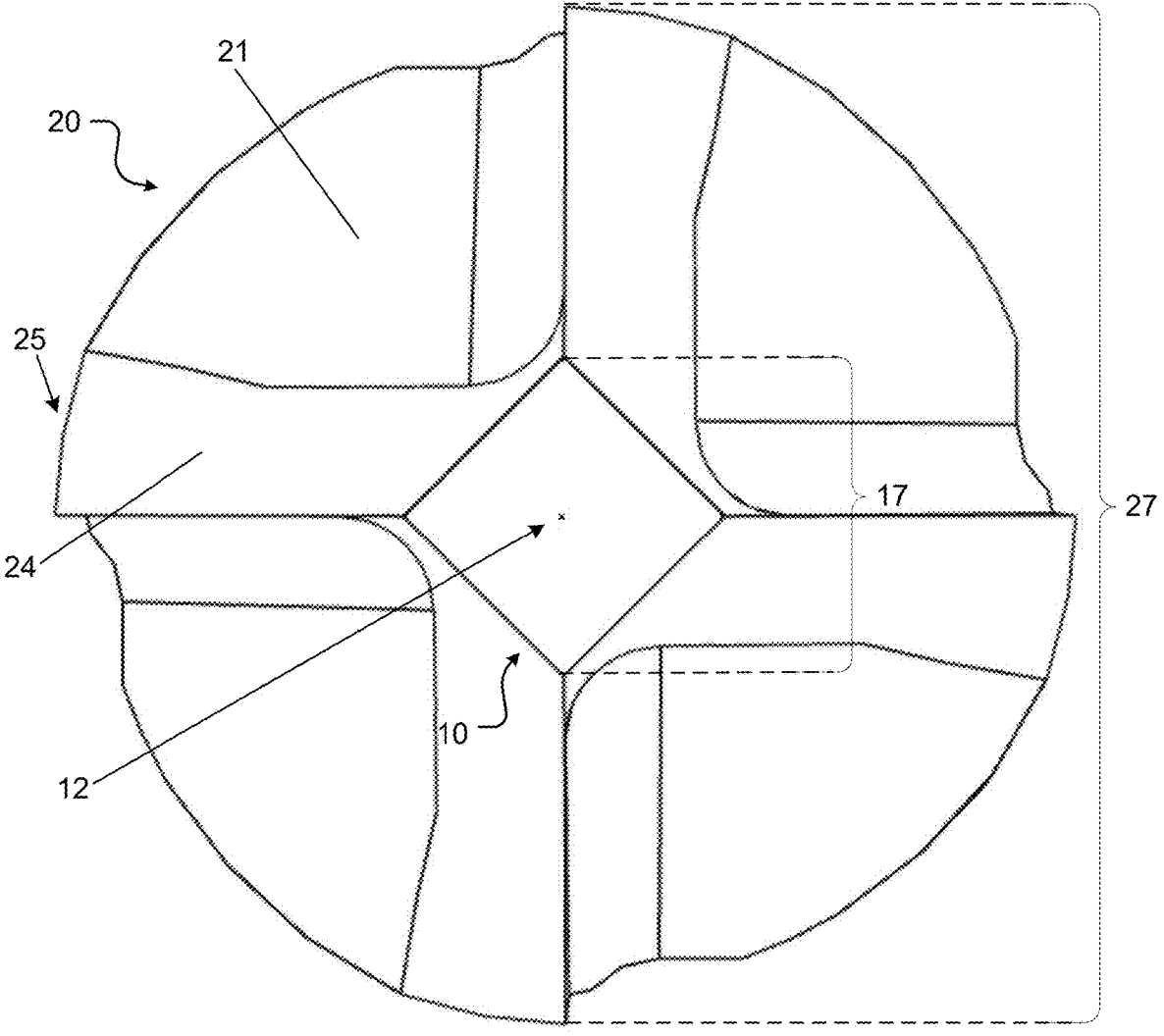
FIG. 3 is a top view of a drill bit according to an embodiment of the present disclosure.

Specifically, referring to FIG. 3, the drilling portion width 17 can be characterized by a ratio between the countersink width 27 and drilling portion width 27. If the drilling portion width 17 were exceedingly smaller than the countersink portion width 27 (e.g., ratio between countersink portion width 27 and drilling portion width 17 is greater than 20) then the drilling portion 10 would not sufficiently guide the countersink portion 20. Namely, the countersink portion 20 would readily override any guidance created by the drilling portion 10. The drilling portion 10 would also not guide the countersink portion 20 if the drilling portion width 17 were greater than the countersink portion width 27. Rather, the countersink portion 20 would be free to move, shift and/or misalign within the cavity created by the drilling portion.

Accordingly, the present embodiment comprises a ratio between the countersink width 27 and drilling portion width 17 between 1 and 10. In some embodiments, the ratio between the countersink width 27 and drilling portion width 17 is between approximately 1 and 6, or between approximately 2 and 6, or between approximately 3 and 6, or between approximately 4 and 6. In further embodiments, the ratio between the countersink width 27 and the drilling portion width 17 is between approximately 3 and 3.5, or between approximately 3.5 and 4, or between approximately 4 and 4.5, or between approximately 4.5 and 5, or between approximately 5 and 5.5, or between approximately 5.5. and 6. Further, as previously discussed, the transition between the countersink portion 20 into the drilling portion 10 lacks a discrete step (i.e., a discrete change from the countersink width 27 to the drilling portion width 17) but is rather a smooth transition defined by at least one transition surface 24. This smooth transition into the drilling portion width 17 encourages alignment of the countersink portion 20 when the countersink portion 20 enters bone. Accordingly, impact to surrounding bone and tissue is mitigated. To further mitigate collateral impact, the drilling portion 10 may be tapered, as shown in FIGS. 1, 2, and 4.

Figure 4:
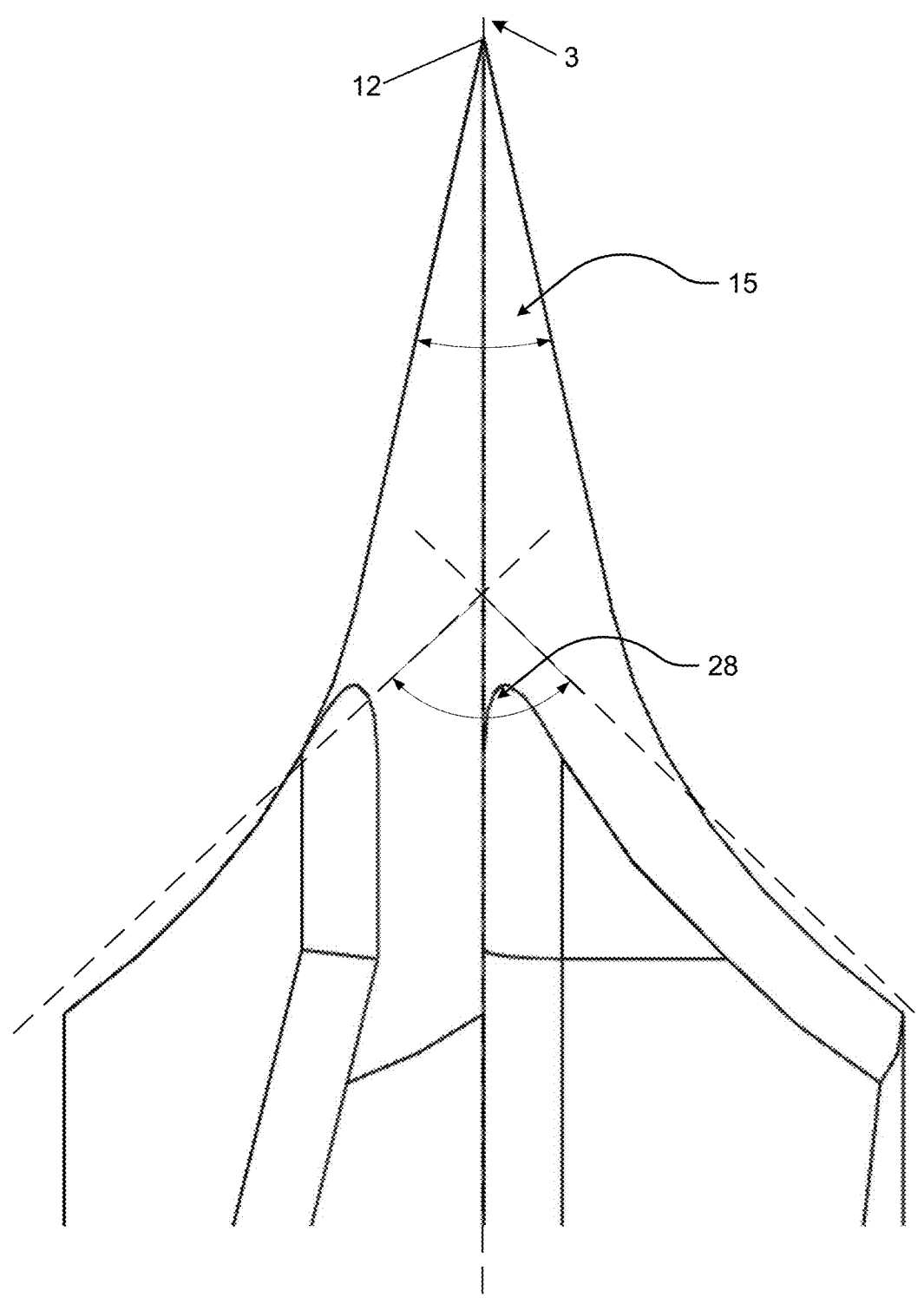
FIG. 4 is a front view of a segment of a drill bit according to an embodiment of the present disclosure.

For example, as shown in FIG. 4, the drilling portion 10 tapers from the drilling portion base 16 to the tip 12. Specifically, the drilling portion 10 taper may define a drill point angle 15, wherein the drill point angle 15 establishes the angle created by the drilling portion 10 when entering the drilling surface. Tapering from the drilling portion base 16 to the tip 12 stabilizes entry of the drilling portion 10 into bone and cases the countersink portion 20 into the bone. Namely, the countersink portion 20 enters a wider initial guide established by the drilling portion 10, and progressively enters a narrower guide. This progressively narrowing guide minimizes stress applied by the countersink portion 20 to the bone, thereby mitigating collateral impact and encouraging alignment during drilling.

Further, the drill point angle 15 is sufficiently acute to pierce bone, including non-uniform surfaces such as ridges and protrusions. The drill point angle 15 is further sufficiently acute to provide a minimally invasive entry point establishing a starter, or pilot hole to guide the countersink portion. Namely, the drill point angle 15 is between approximately 10 and 30 degrees. In some embodiments, the drill point angle 15 is between approximately 10 and 20 degrees. In further embodiments, the drill point angle 15 is between approximately 10 and 12 degrees, or between approximately 12 and 14 degrees, or between approximately 14 and 16 degrees, or between approximately 16 and 18 degrees, or between approximately 18 and 20 degrees. The acute drill point angle 15 defines a sufficiently sharp, or pointed, drilling portion that can both pierce the drilling surface and guide the countersink portion 20 while mitigating collateral impact. The magnitude of potential collateral impact, and thus the need to mitigate such impact, may depend on the implant size and the corresponding countersink size.

Specifically, the present embodiment may comprise a countersink portion 20 sized to create a cavity for large dental implants. For example, in some embodiments, the countersink portion 20 is operable to create a cavity for approximately 6 mm, or approximately 7 mm, or approximately 8 mm, or approximately 9 mm, or approximately 10 mm wide implants. Generally, the countersink portion 20 may be operable to create a countersink diameter between approximately 6 mm and 10 mm wide. In alternative embodiments, the countersink portion 20 may be operable to form a countersink diameter that is less than 6 mm wide while maintaining the advantages disclosed herein. For example, in some embodiments the countersink portion 20 may be operable to create a countersink diameter between 2 mm and 10 mm. Further, the countersink portion 20 creates a chamfered cavity wherein the chamfer is defined by the countersink angle 28. In some embodiments, the countersink angle 28 is between approximately 80 and 120 degrees. In other embodiments, the countersink angle 28 is between 80 and 100 degrees, or between 100 degrees and 120 degrees. In further embodiments, the countersink angle 28 is between 80 and 90 degrees, or between 90 and 100 degrees, or between 100 and 110 degrees, or between 110 and 120 degrees.

Figure 5:
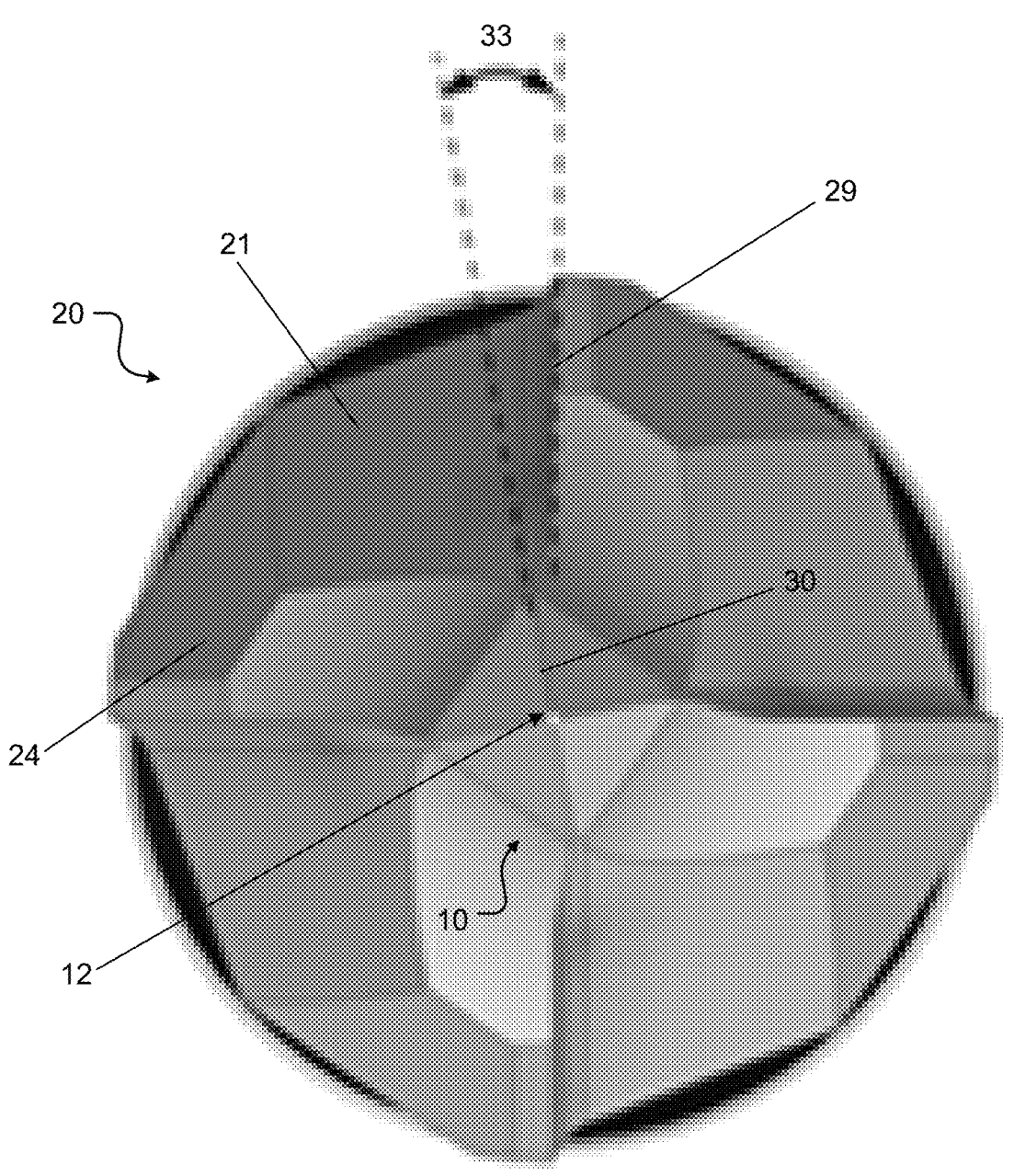
FIG. 5 is a top view of another drill bit according to an embodiment of the present disclosure.
Figure 6:
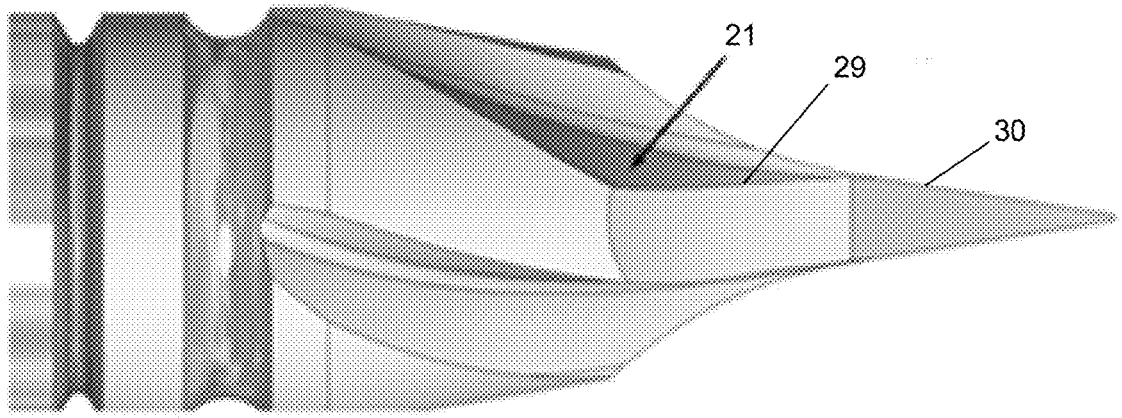
FIG. 6 is a front view of another drill bit according to an embodiment of the present disclosure.
Figure 7:
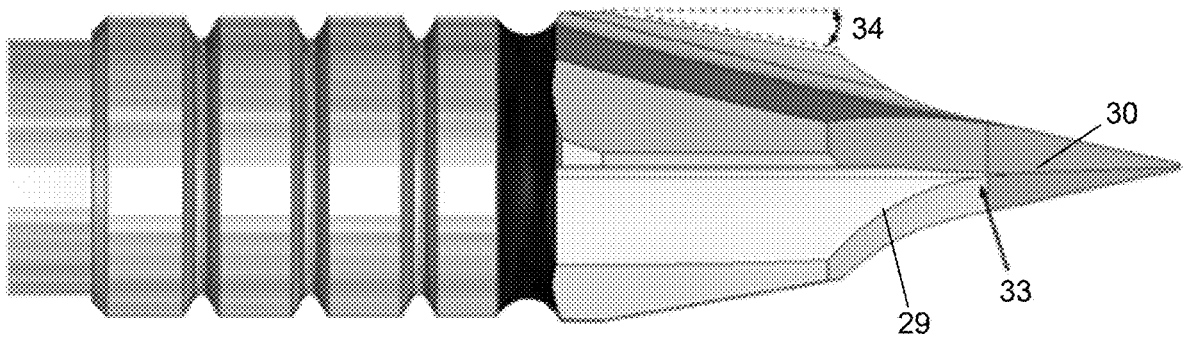
FIG. 7 is a front view of yet another drill bit according to an embodiment of the present disclosure.

FIGS. 5-7 illustrate details of other possible configuration of a drill bit 1. Specifically, and without limitation, FIG. 5 illustrates a drill bit 1 having a flute 21 that extends at least partially into the transition surface 24 and other parts of the drilling portion 10. In some embodiments, cutting efficiency of the drilling portion 10 can be improved by providing a radial offset 33 between the flute 21 and drilling portion tip 12. More specifically, a radial offset 33 may be provided between a flute edge 29 and a point edge 30. Providing the radial offset 33 between the flute 21 and drilling portion tip 12 can provide additional relief to the drill bit 1 to reduce resistance as the drilling portion 10 enters the material being drilled. The radial offset 33 may be on any suitable angle between 0 degrees and 20 degrees. As shown in FIG. 5, the radial offset 33 may correspond to an angle defined between the flute edge 29 and the point edge 30 having an origin at the drilling point top 12.

FIGS. 6 and 7 illustrate additional possible configurations of the drill bit 1 where the flute 21 is provided as a helical flute 21. It should be appreciated that the helical flute 21 can correspond to a right-handed helical flute 21 or a left-handed helical flute 21 without departing from the scope of the present disclosure.

The utilization of a helical flute 21 and the radial offset 33 may also help to create relief for the drilling portion 10 and/or transition surface 24. Additionally, as shown in FIG. 7, a countersink taper 34 may be provided along at least a portion of the ridge 22. Thus, at least some of the countersink portion length 23 may be tapered before reaching the flute 21.

A large countersink size (i.e., to accommodate wide diameter implants) may increase the risk of collateral impact to surrounding bone and soft tissue during surgery. This collateral impact may cause downstream effects on tooth health, such as bone deterioration. Accordingly, the features described above combine to facilitate wide implant insertion while mitigating damage to surrounding bone and soft tissue.

Additionally, various features/components of one embodiment may be combined with features/components of another embodiment. For example, features/components of one figure can be combined with features/components of another figure or features/components of multiple figures. To avoid repetition, every different combination of features has not been described herein, but the different combinations are within the scope of this disclosure. Additionally, if details (including angles, dimensions, etc.) about a feature or component are described with one embodiment or one figure, then those details can apply to similar features of components in other embodiments or other figures.

Moreover, though the present disclosure has included description of one or more embodiments and certain variations and modifications, other variations, combinations, and modifications are within the scope of the disclosure, e.g., as may be within the skill and knowledge of those in the art, after understanding the present disclosure. It is intended to obtain rights which include alternative embodiments to the extent permitted, including alternate, interchangeable, and/or equivalent structures, functions, ranges, or steps to those claimed, regardless of whether such alternate, interchangeable, and/or equivalent structures, functions, ranges, or steps are disclosed herein, and without intending to publicly dedicate any patentable subject matter.

It is to be appreciated that any feature described herein can be claimed in combination with any other feature(s) as described herein, regardless of whether the features come from the same described embodiment.

The concepts illustratively disclosed herein suitably may be practiced in the absence of any element which is not specifically disclosed herein. It is apparent to those skilled in the art, however, that many changes, variations, modifications, other uses, and applications of the disclosure are possible, and changes, variations, modifications, other uses, and applications which do not depart from the spirit and scope of the disclosure are deemed to be covered by the disclosure.

The foregoing discussion has been presented for purposes of illustration and description. The foregoing is not intended to limit the disclosure to the form or forms disclosed herein. In the foregoing Detailed Description, for example, various features are grouped together in one or more embodiments for the purpose of streamlining the disclosure. The features of the embodiments may be combined in alternate embodiments other than those discussed above. This method of disclosure is not to be interpreted as reflecting an intention that the claims require more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate embodiment.

The invention claimed is:

1. A drill bit comprising:
a countersink portion having at least one flute and at least one ridge, the at least one ridge tapering to at least one inflection, the at least one ridge further extending from the at least one inflection toward a drilling portion, thereby forming at least one smooth and continuous transition surface;
the drilling portion having an elongated pin and a tip, wherein the at least one smooth and continuous transition surface continuously tapers from the at least one ridge to the tip of the drilling portion;
wherein the drilling portion extends from the countersink portion, and wherein a radial offset is provided between the at least one flute and the tip of the drilling portion.

2. The drill bit of claim 1, further comprising a shaft engaging the countersink portion, the shaft comprising a shank.

3. The drill bit of claim 2, wherein the shaft comprises a drill-side end, a shank-side end, and at least one groove proximate the drill-side end.

4. The drill bit of claim 1, wherein the radial offset is between 0 degrees and 20 degrees.

5. The drill bit of claim 1, wherein the countersink portion is operable to form a countersink diameter between approximately 6 mm and 10 mm.

6. The drill bit of claim 1, wherein the countersink portion comprises a countersink angle between approximately 80 and 100 degrees.

7. The drill bit of claim 1, wherein the drilling portion comprises a drill point angle between approximately 10 degrees and 30 degrees.

8. A drill bit comprising:

a countersink portion having at least one flute and at least one ridge tapering to at least one inflection, the at least one ridge further extending from the at least one inflection toward a drilling portion thereby forming at least one smooth and continuous transition surface;

the drilling portion having a tip at a distal end of the drill bit, and a base proximate the countersink portion, and wherein a radial offset is provided between the at least one flute and the tip of the drilling portion;

wherein the drilling portion extends from the countersink portion, the drilling portion tapers from the drilling portion base to the tip of the drilling portion, the at least one smooth and continuous transition surface continuously tapers and extends between the countersink portion and the tip of the drilling portion, and a ratio of a length of the countersink portion to a length of the drilling portion is between 1 and 5.

9. The drill bit of claim 8, wherein the drilling portion taper comprises a drill point angle between approximately 10 and 30 degrees.

10. The drill bit of claim 8, further comprising:

a countersink portion base engaging a shaft, the countersink portion base having a countersink portion base width; and a drilling portion base width;

wherein a ratio between the countersink portion base width and the drilling portion base width is between approximately 1 and 10.

11. The drill bit of claim 8, wherein the at least one flute comprises a plurality of flutes.

12. The drill bit of claim 8, wherein the countersink portion is operable to form a countersink diameter between approximately 6 mm and 10 mm.

13. The drill bit of claim 8, wherein the at least one smooth and continuous transition surface forms part of the drilling portion.

14. The drill bit of claim 8, wherein the drilling portion taper comprises a substantially linear portion.

15. A drill bit comprising:

a countersink portion having at least one flute, a plurality of ridges, and a countersink portion base, the plurality of ridges taper to a plurality of inflections, the plurality of ridges further extend from the plurality of inflections toward a drilling portion thereby forming a plurality of smooth, continuous, and concave transition surfaces, wherein the smooth, continuous, and concave transition surfaces continuously taper from the plurality of ridges to a tip of the drilling portion;

the drilling portion extending from the countersink portion, the drilling portion tapering from a drilling portion base tangent the countersink portion to the tip at a distal end of the drill bit, and wherein a radial offset is provided between the at least one flute and the tip of the drilling portion; and a shaft extending from the countersink portion, the shaft having a shank.

16. The drill bit of claim 15, wherein the at least one flute further comprises at least three flutes.

17. The drill bit of claim 15, wherein the drilling portion taper comprises a substantially linear portion.

18. The drill bit of claim 17, wherein the drilling portion taper comprises a drill point angle between approximately 10 and 30 degrees.

19. The drill bit of claim 15, wherein a ratio of a width of the countersink portion base to a width of the drilling portion base is between 1 and 5.

20. The drill bit of claim 15, wherein the countersink portion is operable to form a countersink diameter between approximately 6 mm and 10 mm.

* * * * *